United States Patent
Kirchhuebel

(10) Patent No.: US 7,092,152 B2
(45) Date of Patent: Aug. 15, 2006

(54) OPTICAL DEVICE FOR RELEASABLE ATTACHMENT TO A MICROSCOPE

(75) Inventor: Rainer Kirchhuebel, Asslar (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 313 days.

(21) Appl. No.: 10/671,349

(22) Filed: Sep. 25, 2003

(65) Prior Publication Data
US 2005/0225848 A1    Oct. 13, 2005

(30) Foreign Application Priority Data
Oct. 11, 2002   (DE) ........................... 202 15 635 U

(51) Int. Cl.
G02B 21/00    (2006.01)
(52) U.S. Cl. ........................ 359/381; 359/823; 351/216
(58) Field of Classification Search ...................... None
See application file for complete search history.

(56) References Cited

U.S. PATENT DOCUMENTS

| | | | |
|---|---|---|---|
| 4,575,199 A | 3/1986 | Lisfeld | |
| 4,856,872 A | 8/1989 | Spitznas et al. | ............ 359/826 |
| 5,056,902 A | 10/1991 | Chinnock et al. | ........... 359/503 |
| 5,394,043 A * | 2/1995 | Hsia | ............................. 310/90 |
| 5,554,896 A * | 9/1996 | Hogan | ........................ 307/150 |
| 5,825,535 A | 10/1998 | Biber et al. | |
| 6,212,006 B1 | 4/2001 | Reiner | |
| 6,788,455 B1 | 9/2004 | Kirchhuebel et al. | |
| 6,967,774 B1 | 11/2005 | Kirchhuebel et al. | |
| 2002/0044256 A1 | 4/2002 | Kirchhuebel | ................ 351/205 |

* cited by examiner

*Primary Examiner*—Arnel C. Lavarias
(74) *Attorney, Agent, or Firm*—Flynn, Thiel, Boutell & Tanis, P.C.

(57) ABSTRACT

A removable optical device with at least one lens for releasable attachment to a microscope suited for contact-free observation of an eye, which can be arranged between the objective of the microscope and the eye in the optical axis of the microscope. A drive device is provided, with which the lens can be adjusted along the optical axis of the microscope, whereby an electric drive motor is integrated in the removable device, which, together with the device, can be detached from the microscope and sterilized by suitable methods.

12 Claims, 5 Drawing Sheets

OPTICAL DEVICE FOR RELEASABLE ATTACHMENT TO A MICROSCOPE

FIELD OF THE INVENTION

The invention relates to an optical device for releasable attachment to a microscope suited for contact-free observation of the eye.

BACKGROUND OF THE INVENTION

In ophthalmology, and particularly with vitreous body surgery, specific devices in combination with correspondingly suited microscopes are used, in order to makes possible a contact-free, wide-angle observation of the eye. In particular, with operations on the eye, optical devices are used, with which the surgeon can observe the movements performed with the operating implements, whereby, by the adjustment of the lens in the region between the objective of the microscope and the eye, focusing in different planes is made possible.

Such a device is known, for example, from EP 11 99 591 A1. With this device, the driving movement of a drive motor provided on the microscope can be transferred with the assistance of a flexible drive shaft on a linear gear provided on the device.

Since the devices are used in the direct operating area in the eye, sterilization of the devices, for example, by heating and aerating in autoclaves is of the greatest importance. One disadvantage associated with the device known from EP 11 99 591 A1 is that for transferring of the drive movement, a relatively rigid drive shaft is required. Based on the rigidity of the drive shaft, this can be fixed only inadequately flexibly along suitable attachment points, so that an unwanted contamination of the shaft by contact with non-sterilized objects, for example, the housing of the microscope, can occur. A further disadvantage of the drive by means of a drive shaft is that the device can be pivoted relative to the microscope only within determined limits, since the drive shaft can snap off easily. In addition, the maximum distance between the drive motor and the device is limited by the drive shaft.

An object of the present invention, therefore, starting from this state of the art, is to propose a new, optical device for releasable attachment to a microscope, whose manipulation and hygienic qualities are improved compared with the known devices.

SUMMARY OF THE INVENTION

According to the present invention, the drive motor for remotely controlled adjustment of the lens in the region between the eye and objective of the microscope is integrated in the device, so that the device is released entirely together with the drive motor from the microscope and by suitable methods, can be sterilized. By the integration of the drive motor in the device, the drive shaft for transmission of the drive moment from the drive motor to the device can be eliminated. In addition, the drive movement required for adjustment of the lens within the device is produced by conversion of electrical energy into mechanical energy.

In order to achieve a sufficient sterilization of the device of the present invention, known methods, for example, autoclave under pressure and temperature effects or steam can be used. These sterilization methods represent a potential risk of damage for the electromechanical components of the electric motor. In particular, damage to the drive motor can result from thermal strain and corrosion. In order to reliably eliminate this type of damage by sterilization methods over long periods of use, the drive motor is encapsulated in a gas- and moisture-sealed housing according to a preferred embodiment of the invention. As a result, the drive motor is insular against the atmosphere of the surrounding environment, so that in the frame of the typical sterilization methods, no gas or moisture can access the electro-mechanical components of the drive motor.

Each opening in the housing for encapsulated accommodation of the drive motor represents a potential source of malfunction, which requires the use of correspondingly suited sealing features, so that also with longer periods of use, gases or moisture can not enter the interior of the housing. Housing openings that are particularly difficult to seal are those through which a drive movement, for example, with the use of a drive shaft provided on the drive motor, is transferred from the interior of the housing outwardly. According to a preferred embodiment, this problem can be solved by use of a contract-free coupling, in particular, a magnetic coupling. This type of contact-free coupling has a drive part and an output part, whereby the drive movement between the drive part and output part is transferred contact-free, for example, by magnetic fields. In order to avoid a housing opening transferring the drive movement of the drive motor from the interior of the housing outwardly, the drive part of the contact-free acting coupling is encapsulated together with the drive motor. The drive part of the contract-free acting coupling, in contrast, is arranged outside of the housing and thereby makes available the drive moment transferred from the drive motor to the drive part of the coupling outside of the housing.

In order to provide the drive motor with electrical energy, an electrical cable can be provided, which passes through an opening in the housing and is connected to the drive motor to be electrically conductive. Since the electrical cable itself transfers no movement, the through opening for entry of the electrical cable can be sealed relatively simply from gases and moisture by suitable sealing means. In addition, electrical cables can be fixed in a simple manner along any principle paths on which the cable is laid. Also, the pivoting of the device relative to the microscope is not prevented by the high flexibility of the electrical cable. For sealing of the sealing gap between the housing and the electrical cable, a sealing ring can be provided, which, for example, is fixed by a suitable press nut.

Alternatively or in addition to the use of a sealing ring, also a sealing coupling can be used for encapsulated sealing of the drive motor in the housing, with which hollow chambers in the interior of the housing can be lined to be gas- and moisture-impermeable. As far as necessary, the sealing compound can be pressed in also under pressure into the housing, in order to reliably fill hollow chambers and to close sealing gaps.

In order to enable application of the sealing compound into the housing in a simple manner, the housing can have at least one fill opening. In this manner, it is possible, in particular, to mount the drive motor first completely in the housing and after conclusion of the mounting, to seal the housing by application of the sealing compound.

Since with the sterilization of the device in normal cases, the electrical connection cable must also be sterilized, preferably a plug suitable for sterilization can be provided on the end of the electrical cable.

Alternatively to using an electrical cable for supply the drive motor with electrical drive energy, also accumulators can be provided on the device, which permit a network free energy supply of the drive motor. If, in addition, also a wireless data transmission to the device is provided, over which the control data necessary for the control of the device can be transmitted, then, apart from the mechanical attachment of the device to the microscope, a complete decoupling between the sterilized parts of the device and the non-sterilized parts of the microscope is provided.

The type of lenses that can be attached to the device of the present invention is essentially as desired. Since, however, the lens is the part of the device that lies closes to the eye, which must be arranged with only minimal distance above the eye, the highest specifications as to the sterility of the lens and lens-adjacent components are required. According to a preferred embodiment, therefore, one-way lenses are used, which together with the holding mechanism provided for attachment of the lens, are disposed of after each operation.

Particularly suited for use on the proposed optical devices are lenses, which are embodied in the form of magnifiers. Preferably, higher-refracting, aspherical magnifiers are used, which project a transversely inverted, upside down image, which is righted and horizontally corrected by either a parallel optical path or alternatively, an inversion system arranged beneath the objective.

In order to enable production with the associated holding mechanism with regard to the only one-time use with justifiable costs, the lens and/or the holding mechanism preferably are made from plastic.

BRIEF DESCRIPTION OF THE DRAWINGS

One embodiment of the device of the present invention is shown in the drawings and will be explained in greater detail by way of example.

In the drawings.

DETAILED DESCRIPTION

Figure 1:
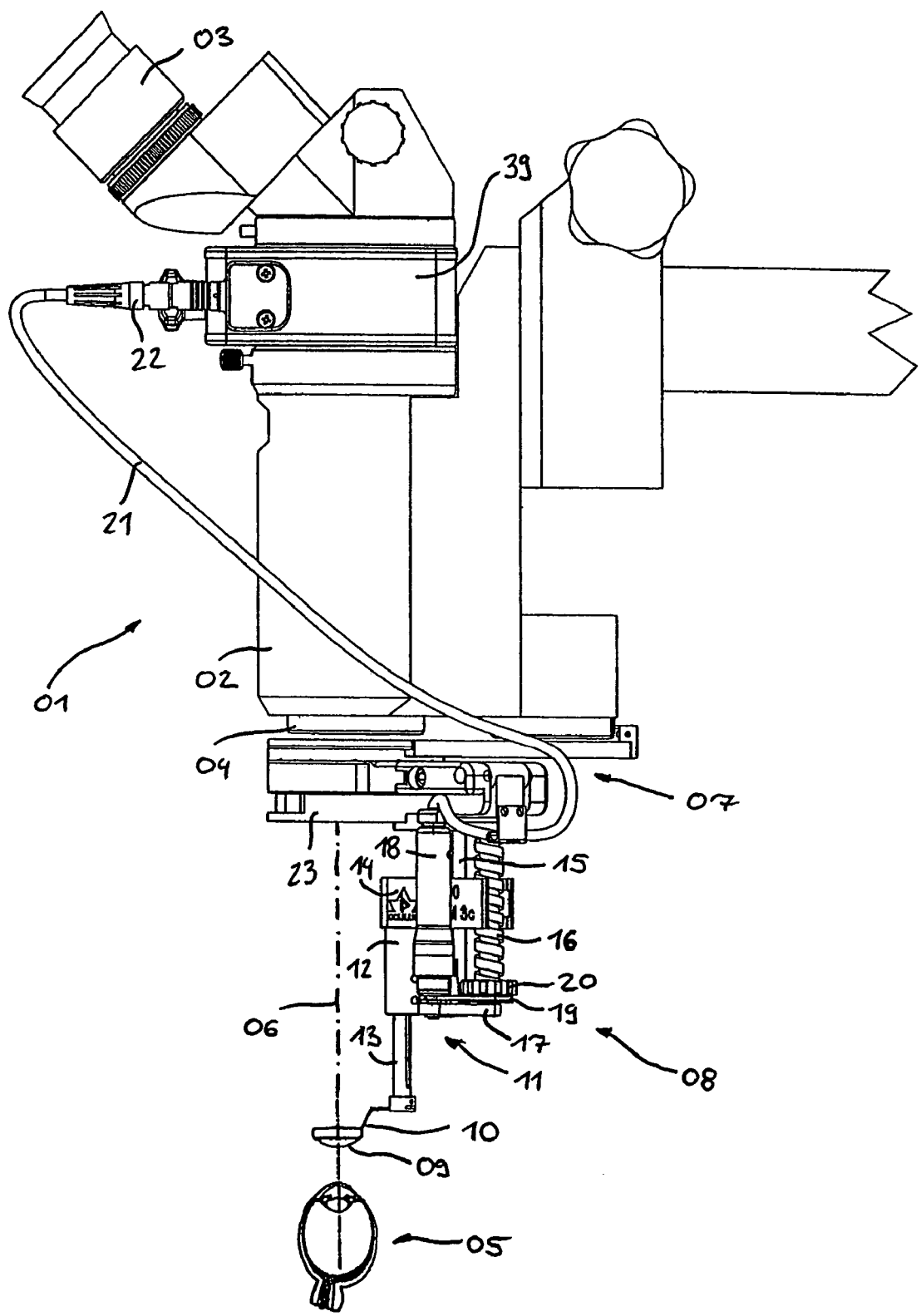
FIG. 1 shows a microscope with an optical device according to the present invention attached thereon in a side view.

In FIG. 1, a microscope 01 with a housing 02, an ocular 03, and an objective 04 is shown. The microscope 01 can be used for wide-angle observation of an eye 05 (represented only schematically) during an eye operation. The optical axis 06 can be oriented to the operating area in the eye 05, in order to enable the enlarged observation of the operating area in the ocular 03.

On the lower side of the housing 02 of the microscope, a holder 07 is attached to the microscope. By means of the holder 07, an optical device according to the present invention can be releasably attached to the microscope 01. The device 08 serves to enable fixing of a lens 09 in the optical path along the optical axis 06. In order to make possible an accurate side to side observation of the movement of the operating instruments in the eye, an inversion prism 39 is also provided in the optical path of the microscope 01. Alternatively thereto, also another suitable inversion device can be used, which also can be arranged beneath the objective 04, for example. The holder 07 can be aligned specifically on the microscope type of different manufacturers, in order to make possible the attachment of similarly constructed optical devices 08 to various microscope types.

The lens 09 can be attached by means of a holding device 10 to a holding arm 11 of the device 08. It is advisable in this regard if the lens 09 and/or the holding device 10 are made of plastic and can be discarded after each individual operation.

The holder arm 11 comprises a guide tube 12 and a telescoping rod 13 elastically supported therein. In this manner, it is permitted that with undesired contact between the eye 05 and the lens 09, the lens 09 can be drawn aside upwardly, so that an injury to the eye is avoided. The holder arm 11 is attached to a traverse 14, which is longitudinally displaceable in the direction of the optical axis 06 on a fixed bar 15 and which is engaged with a threaded spindle 16.

The device 08 is pivotably and rotatably supported on the holder 07, so that the device 08, when needed, can be pivoted out from the optical path of the microscope and, in addition, can be rotated into different positions. The structural details related thereto are known in the art and not specifically shown in the drawings. The threaded spindle 16 is rotatably supported on a base plate 17 and can be rotatingly driven by means of a drive motor 24 (see FIG. 4) arranged in a housing 18 via a drive belt 19. In addition, a handwheel is provided for rotary driving of the threaded spindle 16 by hand, which is non-rotatably connected with the threaded spindle 16.

By the rotating drive of the threaded spindle 16 by means of the drive motor 24 or by means of the handwheel 20, the traverse 14 is lifted or lowered, so that by corresponding adjustment of the lens 09 in the optical path of the microscope 01, focusing in different high planes of the eye 05, is made possible. For supplying the drive motor arranged in the housing 18 with electrical energy, an electrical cable 21 is provided, which can be connected releasably to a voltage source provided in the inversion prism 39 by means of a sterilizable plug 22.

Figure 2:
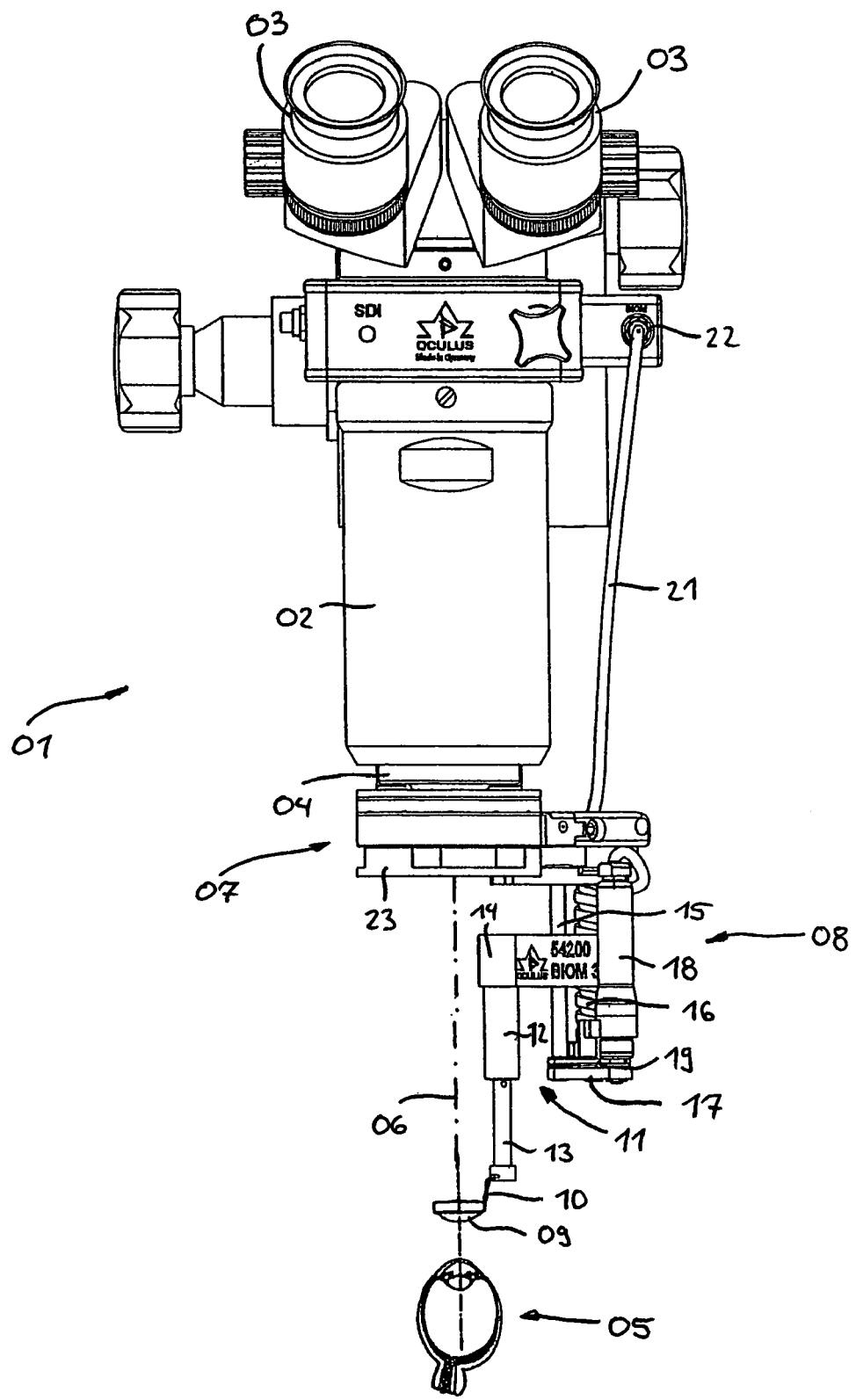
FIG. 2 shows the microscope with the device of the present invention of FIG. 1 in a view from behind.

In FIG. 2, the microscope 01 and the device 08 are shown with the different components in a view from behind.

Figure 3:
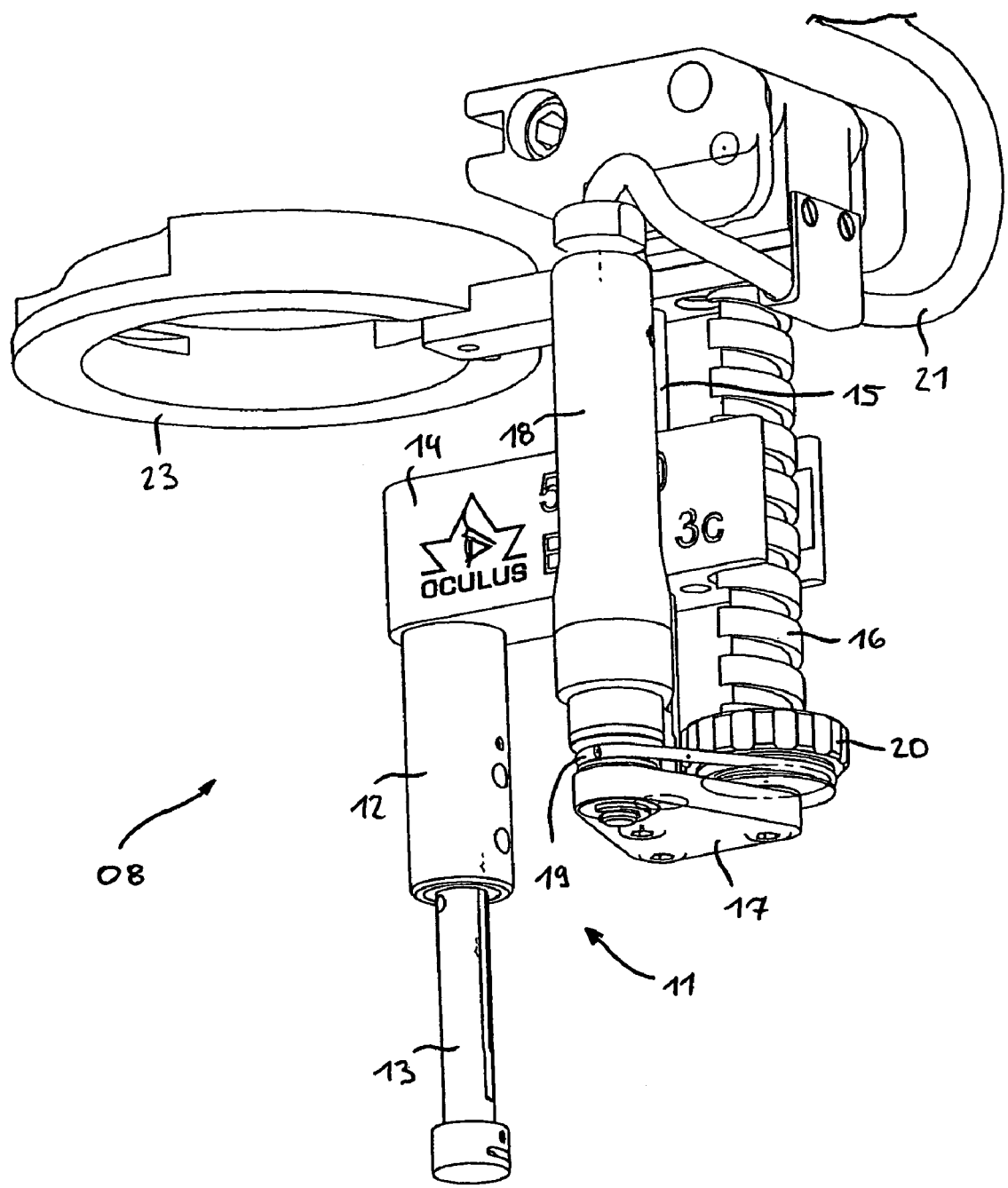
FIG. 3 shows the device according to the present invention in an enlarged perspective view.

FIG. 3 shows the device 08 in an enlarged representation in perspective inclined from below. One recognizes that a holding ring 23 is provided on the device 08, with which additional lenses can be fixed in the optical path of the microscope 01.

Figure 4:
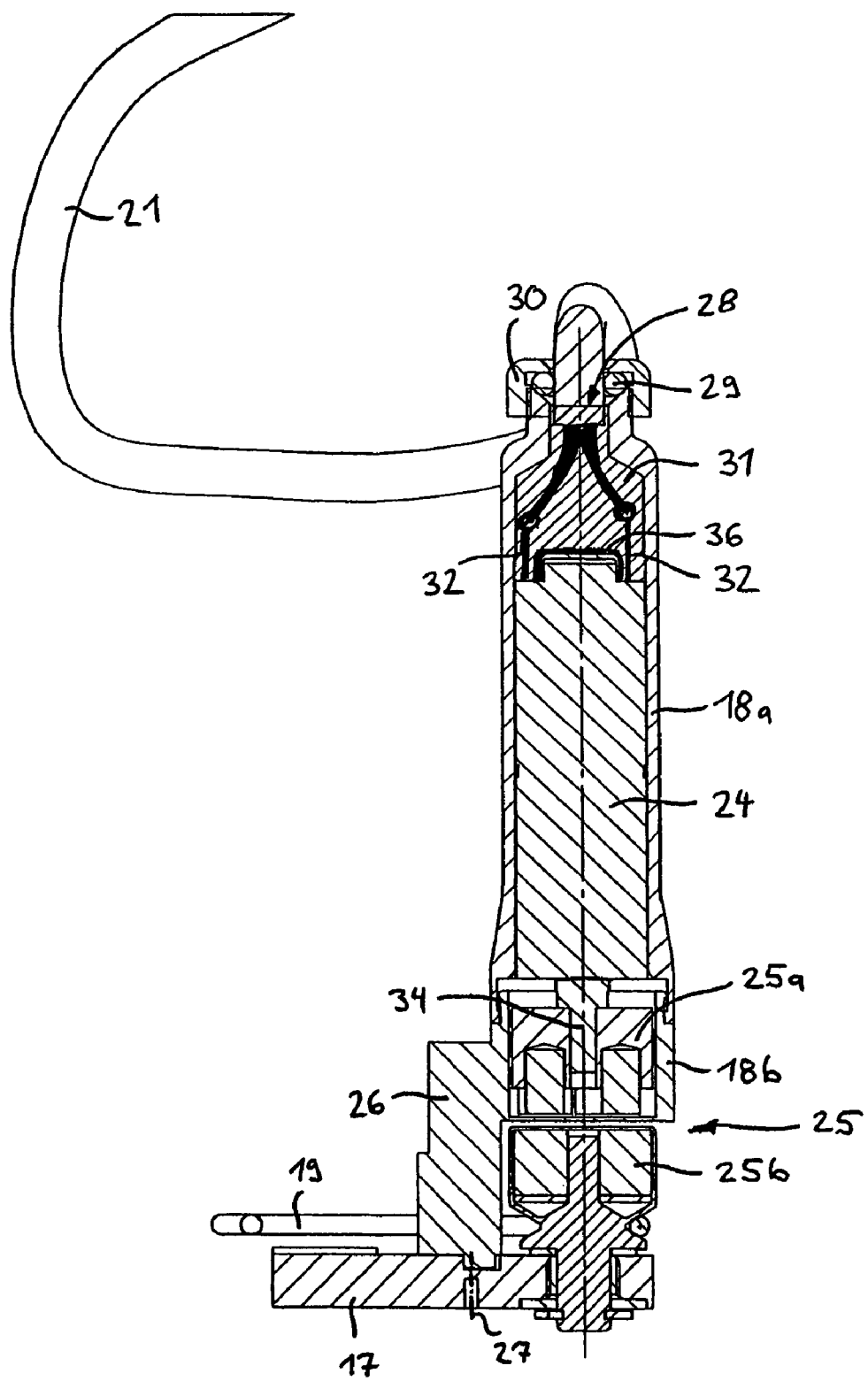
FIG. 4 shows the drive motor of the device according to FIG. 3 in cross section.

In FIG. 4, the encapsulated housing 18 is shown in cross section with the drive motor 24 arranged therein and a magnetic coupling 25 provided for transmitting the drive movement to the drive belt 19. The housing 18 is combined from an upper housing part 18a and a lower housing part 18b, whereby both housing parts 18a and 18b are connected to one another in a gas- and moisture-sealed manner, for example, by adhesive. The lower housing part 18b has an attachment projection 26, with which the housing 18 can be fixed to the base plate 17 by screwing in of an attachment screw 27 to the base plate 17.

The housing 18 has an opening 28 on its upper end for passage of the electrical cable 21 into the interior of the housing 18. The drive motor 24 is shown only schematically in FIG. 4, so that the wire windings of the drive motor 24 are not recognizable in detail. The magnetic coupling 25 comprises a drive part 25a and an output part 25b, on which, respectively, four permanent magnets are provided. The output part 25b of the magnetic coupling is rotatably supported on the base plate 17 outside of the housing 18. The drive part 25a is enclosed within the housing and is non-rotatably connected with the drive shaft of the drive motor 24. If the drive part 25a of the magnetic coupling 25 is rotatingly driven by the drive motor 24, the drive movement produced thereby is transmitted contact-free by the alteration of the magnetic field to the output part 25b. A through opening in the housing 18 for implementation of the adjustment movement produced by the drive motor therefore can be eliminated.

For sealing of the through opening 28, a sealing ring 29 is provided, which is fixed in the sealing gap between the cable 21 and the housing wall of the housing 18 by means of a pressing nut 30 that can be screwed onto the housing 18. In addition, for sealing of the housing 18 in the region above the drive motor 24, in which the electrical connection between the drive motor 24 and the different lines of the cable 21 is made, is lined with a sealing compound 31.

Figure 5:
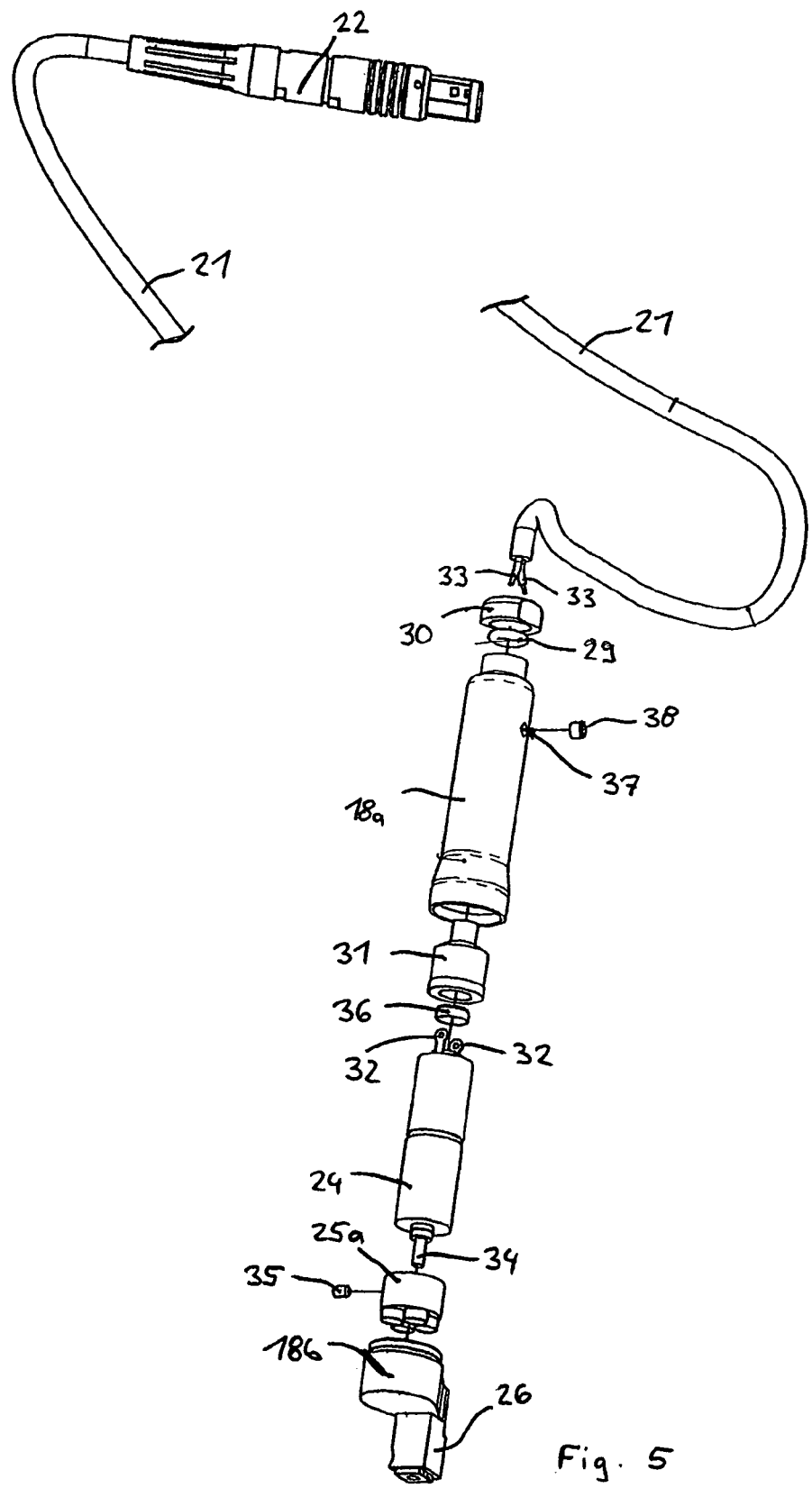
FIG. 5 shows the drive motor of the device according to FIG. 3 in an exploded representation.

FIG. 5 shows the drive motor 24 and the housing 18 in an exploded view. One recognizes the cable 21 with the plug 22 attached thereon, which is suitable for sterilization. On the drive motor 24, two connection terminals 32 are provided, on which the line ends of the electrical lines 33 guided in the cable 21 can be soldered. The drive shaft 34 of the drive motor 24 is non-rotatably attached by means of a threaded pin 35 on the drive part 25a of the magnetic coupling 25. The upper end of the drive shaft 34 is covered outwardly with a corrugated covering 36.

In FIG. 5, the sealing compound 31 is shown in a hardened state. It should also be noted, however, that the sealing compound 31 is not added as a hardened component in the housing 18. In addition, the drive motor 24 is first completely electrically and mechanically mounted in the housing 18 and next, the housing 18 is closed by application of the sealing ring 29 and the pressing nut 30. Next, the sealing compound 31 is applied in a not yet hardened form in the housing 18, in order to permit a hermetic encapsulation of the drive motor from the outside. For application of the first, still fluid sealing compound 31 in the housing 18 in the upper housing part 18a, a fill opening 37 is provided. Subsequently, the fill opening 37 is closed from outside by screwing into the threaded pin 38.

The invention claimed is:

1. In a removable optical device for releasable attachment to a microscope suitable for contact-free observation of an eye with at least one lens arranged between an objective of the microscope and the eye in the optical axis of the microscope and adjustable with a drive device, with which the lens is movable along the optical axis of the microscope, the improvement wherein an electric drive motor is arranged in a housing that encloses the drive motor against the surrounding environment in a manner sealed from gases and moisture, the housing having at least one hollow interior chamber lined with a hardened sealing compound and at least one fill opening, through which the sealing compound is capable of being inserted in the housing after the mounting of the drive motor in the housing, wherein said drive motor and said housing are integrated in the removable optical device, which is detachable from the microscope for sterilization by a suitable method.

2. The device according to claim 1, wherein the drive movement of the drive motor is transferred to a drive part of a contact-free acting coupling, wherein the drive part of the coupling is arranged together with the drive motor encapsulated in gas- and moisture-sealed manner in the housing, and wherein the drive movement of the drive part can be transferred in a contact-free manner to an output part of the coupling arranged outside of the encapsulated housing.

3. The device according to claim 2, wherein the coupling is embodied in the form of a magnetic coupling.

4. The device according to claim 1, wherein the housing has a through opening for passage of an electrical cable, which is gas and moisture sealed by seal against the surrounding environment.

5. The device according to claim 4, wherein the seal comprises a sealing ring that is attached in a sealing gap between the housing and the electrical cable.

6. The device according to claim 4, wherein on an end of the electrical cable, a plug that is suited for sterilization is provided.

7. The device according to claim 1, wherein the housing comprises at least two housing parts connected to one another in a gas- and moisture-sealed manner.

8. The device according to claim 1, wherein an accumulator for network-free energy supply of the drive motor with drive energy is provided on the device.

9. The device according to claim 1, wherein a device for wireless data transmission is provided on the device.

10. The device according to claim 1, wherein the lens together with a holding device provided for attachment of the lens on the device is embodied in the form of a one-way article.

11. The device according to claim 10, wherein the lens and/or the holding device is made from plastic.

12. The device according to claim 1, wherein the lens is embodied in the form of higher-diffracting, aspherical magnifiers.

* * * * *